United States Patent
Zhao et al.

(10) Patent No.: US 9,642,937 B2
(45) Date of Patent: May 9, 2017

(54) PREPARATION METHOD FOR IMPLANTABLE MEDICAL BIOLOGICAL MATERIALS OF ANIMAL ORIGIN

(71) Applicant: Beijing Biosis Healing Biological Technology Co., Ltd., Beijing (CN)

(72) Inventors: Bo Zhao, Beijing (CN); Zhenjun Wang, Beijing (CN)

(73) Assignee: BEIJING BIOSIS HEALING BIOLOGICAL TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 14/894,537

(22) PCT Filed: Aug. 8, 2013

(86) PCT No.: PCT/CN2013/081050
§ 371 (c)(1),
(2) Date: Nov. 30, 2015

(87) PCT Pub. No.: WO2014/190618
PCT Pub. Date: Dec. 4, 2014

(65) Prior Publication Data
US 2016/0101215 A1    Apr. 14, 2016

(30) Foreign Application Priority Data
May 28, 2013   (CN) .......................... 2013 1 0203603

(51) Int. Cl.
*C12N 7/06*    (2006.01)
*A61L 27/36*   (2006.01)
*C12N 7/08*    (2006.01)

(52) U.S. Cl.
CPC ....... *A61L 27/3687* (2013.01); *A61L 27/3604* (2013.01); *A61L 27/3629* (2013.01); *A61L 27/3633* (2013.01); *A61L 27/3691* (2013.01)

(58) Field of Classification Search
CPC .................. A61L 27/3687; A61L 27/3604
(Continued)

(56) References Cited

FOREIGN PATENT DOCUMENTS

| CN | 1266716 A | 9/2000 |
| CN | 1903382 A | 1/2007 |
| WO | WO2008097885 A2 | 8/2008 |

OTHER PUBLICATIONS

Huo, Yanli: "Acellular Amniotic Emebrane and Small Intestinal Submucosa Promotes Skin Reparation and Vascularizatio", China Pharmaceutical University Master Degree Thesis, Nov. 2009, p. 10.

*Primary Examiner* — Kevin Joyner
(74) *Attorney, Agent, or Firm* — Gokalp Bayramoglu

(57) ABSTRACT

The present invention provides a preparation method for implantable medical biological material of animal origin comprising the following procedures: Pre-processing, and washing of animal tissue materials; inactivation of virus; decellularizing cell; sodium chloride processing; molding and packaging sterilization. Cell-free ECM materials of animal origin produced by this method can achieve the goal of completely removing cell components of animal origin and composition of DNA, and at the same time, the natural ECM composition, three-dimensional structure and active growth factor which can induce and promote tissue regeneration retain. By using this process, endotoxin, organic solvents and toxic solvent residue are thus omitted and products with different sizes, thickness and mechanical strength can be formed.

20 Claims, 2 Drawing Sheets

PREPARATION METHOD FOR IMPLANTABLE MEDICAL BIOLOGICAL MATERIALS OF ANIMAL ORIGIN

FIELD OF THE INVENTION

The present invention relates to medical biological material field, and more particularly to a preparation method for implantable medical biological material of animal origin.

BACKGROUND OF THE INVENTION

A variety of diseases and trauma would defects of some tissues or organs and the loss of some or all functions, which are one of the major hazard we human beings are facing. Research and development of ideal materials for tissue repairing have become a major issue in the field of medicine, biological sciences and material science. The materials being widely used for tissue repairing in clinical medical are mostly un-absorbable artificial materials, which include polymer materials (such as polypropylene, PTFE, polylactic acid, poly glycolic acid, silica gel, etc.), metal materials (such as stainless steel, titanium and its alloys, etc.), inorganic materials (such as bioactive ceramic, hydroxyapatite, etc.) and composite material (carbon fiber/polymer, the glass fiber/polymer, etc.).

The structure and composition of the above material are far different from body tissues. The un-absorbable artificial materials can only act as an alternative and provide support in the short term. Un-absorbable artificial materials do not have the functions of promoting tissue regeneration and achieving organizational functions. Besides, after the implantation, artificial materials which cannot degrade remain in the body permanently if not surgically removed. Its stability, toxicity and carcinogenicity are difficult to control.

In some developed countries, implantable medical biomaterials are experiencing major industrial revolutions. Biodegradable and new biological materials which can induce tissue generation are taking the place of traditional non-absorbable materials. Based on principle of tissue engineering, extracellular matrix (extracellular matrix, ECM) material which uses animal tissues as raw material is the major trend. ECM is made up of many kinds of macromolecular substances such as collagen, the collagen glycoprotein, the composition such as amino glycan, proteoglycans, elastin, macromolecular substances are constructed in certain proportion form a complex three dimensional organic structure. The complex three dimensional organic structure provides suitable micro environment for the survival and activity of all kinds of cells, thus adjusting the cell growth, shape, metabolism, migration, proliferation and differentiation and regulation of tissue and organ function. A serious consequence due to tissue defect is a loss of "soil" (i.e. the losing of ECM), which is the main reason that the body itself cannot realize tissue repair and regeneration functions. Natural ECM can act as "soil" and is an ideal tissue repairing material for tissue regeneration. Removing the cell ingredient of animal tissue can result in the failure of most of the immunogenicity of the cellular elements, and the ECM components thus remain. An ideal tissue repairing material is then developed.

In clinical application abroad, there are cell-free ECM materials such as leather, pericardium, small intestine of animal origin products that are derived from animals such as pigs, horses and cattle. Among them, cell-free small intestinal submucosa (small intestinal submucosa, SIS) material is the most ideal soft tissue repairing material as is acknowledged in academia field. Cell-free SIS matrix material has the advantages below:

1) Low immunogenicity and high histocompatibility;
2) Special structure and composition to actively induce all kinds of tissue regeneration and form the biological basis;
3) Wide application field. It can be applied to various soft tissue repairing of human body;
4) Antimicrobial activity. The cell-free SIS substrate materials of American Cook Biotech Incorporated have clinical application of many samples in the abdominal wall repair, burns, anal fistula, refractory wound, plastic surgery, pelvic floor repair, tendon repair, genitourinary tract repair, nerve repair, and other fields.

There are lots of domestic and foreign patents and literature reports concerning the preparation of cell-free SIS matrix material, but only the company Cook Biotech incorporated cell-free SIS matrix material products in clinical application.

Cell-free process and inactivated virus process are the main processes and technical difficulties when it comes to preparing cell-free SIS matrix materials. The process requires a complete removal of virus in the small intestinal submucosa, cell composition and animal origin ingredient of DNA. At the same time, the process requires a complete reservation of the natural ECM composition and three-dimensional structure. In particular, the growth factors (such as alkaline growth factors, transforming growth factor, etc.) should be reserved to promote tissue regeneration. Reported method of cell-free and virus inactivated methods vary, but most of them cannot remove all the DNA ingredients of animal origin completely, are time-consuming and need to use a variety of organic solvent and high strength alkali, which leads to a destruction of the active composition of extracellular matrix cell-free SIS. Harmful solvent residues cause cell toxicity, thus altering the effect of tissue repairing. In addition, most of the technologies cannot take effective measures to control endotoxin residues. Cell-free SIS molding process is another technical difficulty of the preparation of matrix materials. In the molding process, the small intestine has only 6~8 cm cross-section and the thickness of the small intestinal submucosa is less than 0.1 mm. It is difficult to produce tissue repairing products that are of different size and thickness, and which can be adapted to different requirements of mechanical strength. Cook Biotech Incorporated uses the method of vacuum pressing molding. This method compresses the space structure of decellularized SIS matrix material and destroys the natural ECM's three-dimensional structure, thus influencing the porosity of this material.

A clinical study has shown that the cell-free SIS matrix material products (surgisis BIODESIGN etc.) produced by Cook Biotech Incorporated caused syndromes in the clinical application such as serious swelling, infections, immune rejection, and complications such as poor healing of organization. Among those syndromes, the highest occurring is swelling. Complications may lead to disease recurrence or even to a need of a second operation to remove cell-free SIS matrix materials which have already been implanted. Studies have proven that serum swelling is caused by Th2 inflammatory cytokine responses, and the reaction is closely related to the products of animal origin residual DNA.

BRIEF DESCRIPTION OF THE INVENTION

This present invention is to provide a preparation method for implantable medical biological materials of animal origin. Cell-free ECM materials of animal origin produced by this method can achieve the goal of completely removing cell components of animal origin and composition of DNA, and at the same time, the natural ECM composition, three-dimensional structure and active growth factor which can induce and promote tissue regeneration can be retained. By using this process, endotoxin, organic solvents and toxic solvent residue are thus removed and products with different sizes, thickness and mechanical strength can be formed.

The present invention adopts the below technical resolution:

A preparation method for implantable medical biological material of animal origin, comprising:

1) Pre-Processing, Separation and Washing of Animal Tissue Materials

Acquiring fresh animal tissue and washing the animal tissue 3 times by using normal saline. The animals referred above theoretically include all animals. In one preferred embodiment, the animal is selected from the group consisting of pigs, cattle and horses. Pig is considered to be the most preferable animal. The tissue is selected from the group consisting of small intestinal submucosa, genuine leather and the pericardium.

3). Inactivation of Virus

Inactivating the virus by using the method of ethanol solution with low concentration of peracetic acid. This cleaning step is conducted in the oscillation ultrasonic cleaners with constant temperature. Peracetic acid takes up the percentage of 0.05~0.2% by volume (with 0.1% preferred) and the inactivation time is set at 1~2 h (preferably for 1 h). The oscillation frequency of cleaners is set at 30~600 RPM (preferably for 100~300 RPM, 200 RPM is considered to be the best). The ultrasonic frequency is set at 20~80 KHZ (preferably 20~50 KHZ, further preferably 35~50 KHZ, most preferably for 45 KHZ). The temperature ranges from 4~40° C. For cleaning the inactivated materials for 2~5 times in phosphate buffer, each of the cleaning processes is set at 15 minutes. Detecting the pH value of the phosphate buffer after the cleaning process. When the pH reaches 6.5 to 7.5, cleaning the above processed material with flow injection water, this cleaning process is terminated when a detection of conductivity is 1.5 um/s. Preparation of phosphate buffer is achieved by dissolving 7.9 g NaCl, 0.2 g KCl, 0.24 g KH2PO4 and 1.8 g K2HPO4 into 800 ml distilled water, and adjusting the pH value by adding HCl solution to achieve a pH value of 7.4, then adding distilled water until the constant volume reaches 1 L.

3. Decellularized Cell

The cleaning step is conducted in the oscillation sink having ultrasonic cleaners with constant temperature. First of all, materials are placed into the oscillation sink for cleaning, then sodium hydroxide solution is injected into the oscillation sink, placing the cleaners into working mode. The cleaning time is set at 5~30 min (preferably for 20 min), the sodium hydroxide solution concentration is 5~100 mmol/L (preferably for 5~20 mmol/L, further preferably 10 mmol/L). Then, cleaners in off mode are placed and sodium hydroxide solution is poured out. Phosphate buffer solution is injected into the cleaner and the cleaner is placed into open mode. The cleaning time is set at 5~20 minutes (preferably for 15 min), repeating the phosphate buffer cleaning process for about 2~5 times, detecting the pH value of the phosphate buffer solution after cleaning. When the pH value of the detected phosphate buffer solution is in the range from 6.5 to 7.5, the processed material is cleaned by using the flowing water for injection. The flowing water cleaning process is terminated when a conductivity is 1.5 um/s is detected. The oscillation frequency of the cleaning step is set at 100~300 RPM (preferably for 200 RPM), ultrasonic frequency ranges from 20~80 KHZ (preferably 20~50 KHZ, further preferably of 35~50 KHZ, most preferably for 45 KHZ). The preparation of phosphate buffer solution can be obtained as in step 2.

4. Sodium Chloride Processing

This step is conducted in an oscillation sink having an ultrasonic cleaners with constant temperature. Materials are placed into the oscillation sink for cleaning, and then sodium chloride solution is injected into the oscillation sink, placing the cleaners into working mode. The cleaning time is set at 5~30 min (preferably for 20 minutes). The sodium chloride solution concentration is 0.015 mol/L or 2 mol/L (preferably 0.015 mol/L). The pH value is less than 7.8. Then the materials are washed with flowing injection water and the conductivity of the cleaning water is detected. The washing step is terminated when the detected cleaning water is 1.5 um/s. The oscillation frequency of the cleaning sink in the cleaning step is 100~300 RPM (further optimization for 200 RPM). The ultrasonic frequency ranges from 20~80 KHZ (preferably 20~50 KHZ, further preferably 35~50 KHZ, the optimal frequency is 45 KHZ).

5. The Molding Step

This step further comprises the following three steps: fixture of the devices, freezing and drying and micro hole punching using laser. The sizes and shapes of the devices (preferably stainless steel) vary in accordance with different product requirements. The material is fixed on the device. Layers of the material may overlap according to different product requirements. Material which has been washed with flowing injected water is placed and fixed on the device into freeze drying machine. The lyophilization process is performed as pre-designed. The pre-designed lyophilization process is as following: pre-cooling the material to −25~−50° C. (preferably for −25° C.); conducting a heat conservation of the material for 0.5~4 hours (preferably for 2 h); rising a temperature of 15° C. and conducting a heat conservation of the material for 4~12 hours (preferably for 8 h); rising a temperature of 15° C. and conducting a heat conservation of the material for 0.5~4 hours (preferably for 2 h); rising the temperature up to 25° C. and conducting a heat conservation of the material for 4 hours. After the lyophilization process, by using laser, micro holes are punched on the lyophilizated material. The aperture of the lyophilizated material ranges from 0.05~1 mm (preferably 0.2~0.5 mm). The space between the holes range from 0.1~2 cm (preferably 0.5~1 cm). The laser micro hole drilling referred above is the use of laser technology, which can drill the material with micron grade holes. By using a laser micro hole drilling machine, a pore formation may be achieved on the surface of the material, which is beneficial to tissue repairing.

6. Packaging Sterilization

The packaging step is performed in sterile conditions. One layer of the packaging is tyvek paper, the other layer is polyethylene plastic. After packaging, ethylene oxide sterilization is performed.

The injection water of this invention follows the provisions of the state pharmacopoeia standards.

The oscillation cleaning sink having ultrasonic cleaner is the combination of the traditional ultrasonic cleaning sink with mechanical oscillators. This combination makes mechanical oscillation and ultrasonic cleaning function at the same time, realizing the mechanical oscillation and ultrasonic cleaning functioning together.

The present invention relates to a preparation method for implantable medical biological material of animal origin. It can be used for the preparation of cell-free small intestinal submucosa matrix material, decellularized dermal matrix material, and cell-free pericardium substrate materials.

Compared to the existing technology, the present invention has the following advantages and beneficial effects: the present invention uses an oscillation sink having ultrasonic cleaner, mechanical oscillation and ultrasonic cleaning functioning together, thus improving the efficiency of animal cells inactivated virus in the ECM material preparation technology, process and cleaning of animal origin and the DNA. The processing time is greatly reduced and the technological process is simplified. The whole process of preparation only uses three solutions (i.e. peracetic acid, sodium hydroxide and sodium chloride solution) and the concentration of the above three solutions are far less than the existing preparation technology. The immunogenicity of the preparation material are fully removed, the natural ECM structure and growth factors and other active ingredients are fully retained. Besides, an innovated combination of freeze-drying technology and laser micro hole drilling technology are applied in the molding process without destroying the structure of natural ECM and effective ingredients like growth factor. Under the premise of not destroying the three-dimensional structure of natural ECM, products having different shapes, sizes, thickness and mechanical strength are thus produced depending on different applications.

DETAILED DESCRIPTION OF THE INVENTION

Figure 1:
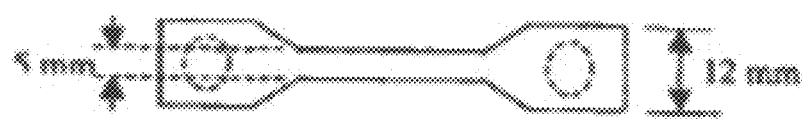
FIG. 1 is a clipping schematic view of the second embodiment.

The present invention is described with the accompanying embodiments but not limited to the embodiment.

First Embodiment

The preparation of substrate material of pig's small intestinal submucosa.

1. Pre-Processing, Separation and Washing of Animal Tissue Materials

Taking out freshly slaughtered pig's small intestine tissue, cleaning and isolating small intestine submucosa, then washing the isolated small intestine submucosa with injection water for 3 times.

2. Inactivation of Virus

Inactivating the virus by using the method of ethanol solution with low concentration of peracetic acid. This cleaning step is conducted in the oscillation ultrasonic cleaners with constant temperature. Peracetic acid takes up the percentage of 0.05~0.2% by volume (preferred for 0.1%) and the inactivation time is 1~2 h (preferably for 1 h). The oscillation frequency of cleaners ranges from 30 to 600 RPM (preferably ranges from 100 to 300 RPM, 200 RPM is considered to be the best). The ultrasonic frequency ranges from 20 to 80 KHZ (preferably ranges from 20 to 50 KHZ, further preferably ranges from 35 to 50 KHZ, most preferably for 45 KHZ). The temperature ranges from 4 to 40° C. Inactivated materials are cleaned for 2~5 times in phosphate buffer, each of the cleaning process being 15 minutes. Detecting the pH value of the phosphate buffer after the cleaning process, when pH reaches 6.5 to 7.5, the above processed material is cleaned with flow injection water until conductivity is detected as being lower than 1.5 um/s. Preparation of phosphate buffer is achieved by dissolving 7.9 g NaCl, 0.2 g KCl, 0.24 g $KH_2PO_4$ and 1.8 g $K_2HPO_4$ into 800 ml distilled water, adjusting the pH value by adding HCl solution to achieve a pH value of 7.4, then adding distilled water until the constant volume reaches 1 L.

3. Decellularized Cell

The cleaning steps are conducted in the oscillation sink having ultrasonic cleaners with constant temperature. First of all, the materials are placed into the oscillation sink for cleaning, and then sodium hydroxide solution is injected into the oscillation sink, turning on the cleaners. The cleaning time is 5~30 min (preferably for 20 min). The sodium hydroxide solution concentration is 5~100 mmol/L (preferably for 5~20 mmol/L, further preferably for 10 mmol/L). Then the cleaners are turned off and sodium hydroxide solution is poured out. Phosphate buffer solution is injected into the cleaner and turning on the cleaner. The cleaning time is 5~20 minutes (preferably for 15 min), repeating the phosphate buffer cleaning process for about 2~5 times, detecting the pH value of the phosphate buffer solution after cleaning. When the pH value of the detected phosphate buffer solution is in the range from 6.5 to 7.5, the processed material by is cleaned by the flowing water for injection. The flowing water cleaning process is terminated when a conductivity lower than 1.5 um/s is detected. The oscillation frequency of the cleaning step ranges from 100 to 300 RPM (preferably for 200 RPM), ultrasonic frequency ranges from 20 to 80 KHZ (preferably 20~50 KHZ, further preferably of 35~50 KHZ, most preferably for 45 KHZ). The preparation of phosphate buffer solution can be obtained as in step 2.

4. Sodium Chloride Treating

This step is conducted in an oscillation sink having ultrasonic cleaners with constant temperature. Materials are placed into the oscillation sink for cleaning, and sodium chloride solution is injected into the oscillation sink, turning on the cleaners. The cleaning time is 5~30 min (preferably for 20 minutes). The concentration of sodium chloride solution is 0.015 mol/L or 2 mol/L (preferably 0.015 mol/L). The pH value is less than 7.8. The materials are washed with flowing injection water and conductivity of the cleaning water is detected. The washing step is terminated when the conductivity of the detected cleaning water is lower than 1.5 um/s. The oscillation frequency of the cleaning sink in this cleaning step ranges from 100 to 300 RPM (preferably for 200 RPM). The ultrasonic frequency ranges from 20 to 80 KHZ (preferably 20~50 KHZ, further preferably 35~50 KHZ, the most preferably is 45 KHZ).

5. The Molding Step

The sizes and shapes of plurality of stainless steel devices vary in accordance with different product requirements. The material is fixed on the stainless steel device. Layers of the material may overlap according to different product requirements. The material which has been washed by flowing injected water is placed and fixed on the device into freeze drying machine. The lyophilization process is performed as pre-designed. The pre-designed lyophilization process is carried out as following: pre-cooling the material to −25~−50° C. (preferably for −25° C.) and conserving for 0.5~4 hours (preferably for 2 h); rising a temperature of 15° C. and conserving for 4~12 hours (preferably for 8 h); rising a temperature of 15° C. and conserving for 0.5~4 hours (preferably for 2 h), rising the temperature up to 25° C. and conserving for 4 hours. After the lyophilization process, laser is used to punch micro holes on the lyophilized material. Aperture of the lyophilized material ranges from 0.05 to 1 mm (preferably 0.2~0.5 mm). The distance between the adjacent two holes ranges from 0.1 to 2 cm (preferably 0.5~1 cm).

6. Packaging Sterilization

The packaging step is performed in sterile conditions. One layer of the packaging is tyvek paper, the other layer is polyethylene plastic. After packaging, an ethylene oxide sterilization is performed.

The Second Embodiment

Testing the physical and chemical properties, histology, growth factors and biological performance of the decellularized small intestinal submucosa matrix material obtained from the first embodiment.

2. Testing the physical properties of the obtained materials having eight layers. The testing items include the following: suture retention, tensile strength, bursting strength and porosity.

1). Suture retention test: 2-0 surgical suture or stainless steel wire of the same diameter is used to stitch on the edge of one end of the eight-layer material and located about 2 mm off the edge, the other end of the suture or stainless steel wire of the eight-layer material is fixed on the tension meter. The wire is being stretched at a speed of 20 mm/min until the suture point is torn. Pulling force is recorded when suture point is torn. 3 batches of samples are tested according to the above method under the same condition. Results show that the suture tensile strength is greater than or equal to 5±0.5 N.

2). The tensile strength testing method: tensile (compressed) tester is used, as shown in FIG. 1. Eight-layer materials are cut into samples. The humidity of the materials after cutting ranges from 40% to 60%. Samples are placed under the temperature of 22° C.±2° C. for 2 hours and tested immediately thereafter. Two ends of the sample are fixed onto clamp heads of tensile testing machine and the sample is tested at a speed of 100 mm/min until the sample fractures. The samples are tested transversely and longitudinally respectively. The force when the sample is broken is recorded with a unit of N. 3 batches of the above samples are tested under the same condition. Results show that longitudinal force is 15 N and the transverse force is 8 N.

3). Bursting strength testing:

using the tensile (compressed) tester, the eight-layer materials are cut into 23*23 mm square samples for spare use. Cut materials are placed under the condition where the relative humidity of cut material ranges from 40% to 60% and the temperature is 24° C.±2° C. for 2 hours. Experiment is conducted immediately thereafter. Samples are secured to the stretcher workbench with ring clamps, making the spherical probe pass through the samples at a speed of 750 mm/min. Force when the samples are worn out is recored. Three batches of samples are tested according to the above method. Results show that the bursting strength is greater than 120 N.

4). Porosity determination: determining the porosity of the material by mercury injection method. Results show that the porosity is not less than 85%.

2. Testing the chemical performance of the eight-layer materials obtained from above process, wherein the testing items include viruses, pH value, residues of endotoxin and DNA.

1) Preparation of testing liquids: homogeneous thickness parts of the sample are taken; the sample is cut into debris with an average area of 1 cm$^2$; cut samples are washed with water and sample is dried. Then sample is placed into a glass container, water is added into the glass container, wherein the ratio between the total surface area of the sample (cm2) and the volume of water (mL) is 5:1. Glass container is covered and the glass container is placed into a pressure steam sterilizer. Above sample is heated at a temperature of 121° C.±1° C. for 30 minutes. Sample and liquid are separated after heating. Heated liquid is cooled to room temperature as test fluid. The same volume of water is taken as a blank comparison.

2) Virus detection: Pseudorabies are taken as the indicate virus; detecting the DNA copy number of viruses through real-time and quantitative PCR method. Three batches of samples are detected. Results show that the viral DNA copy number is 0.

3). pH value testing: experiment is conducted according to the regulations published in GB/T14233.1 (the medical infusion, transfusion, injection equipment checking method 1th part: methods of chemical analysis) method specified in 5.4.1. Results show that the pH value difference between the test solution and control solution is less than 1.5.

4). Endotoxin: Every 6 cm$^2$ of samples should mix with 1 ml extraction medium. The experiment is conducted under the temperature of 37±1° C. for 72±2 hours. The extraction medium is saline solution. The experiment is conducted following the regulations published in GB/t 14233, which are the medical infusion, transfusion, injection equipment checking method 2nd part: biological test methods), and testing three batches of samples. Results show that the endotoxin content is less than 5 EU/g.

5) Detection of DNA residual: Samples obtained from the first embodiment are detected based on biological agents' residual DNA detection method (the Chinese Pharmacopoeia 2010, Appendix method for determination of IX-B residues of exogenous DNA) by a fluorescence staining method. Results show that the residues of DNA materials do not exceed 150 pg/g.

3. Histological Detection

Figure 2:
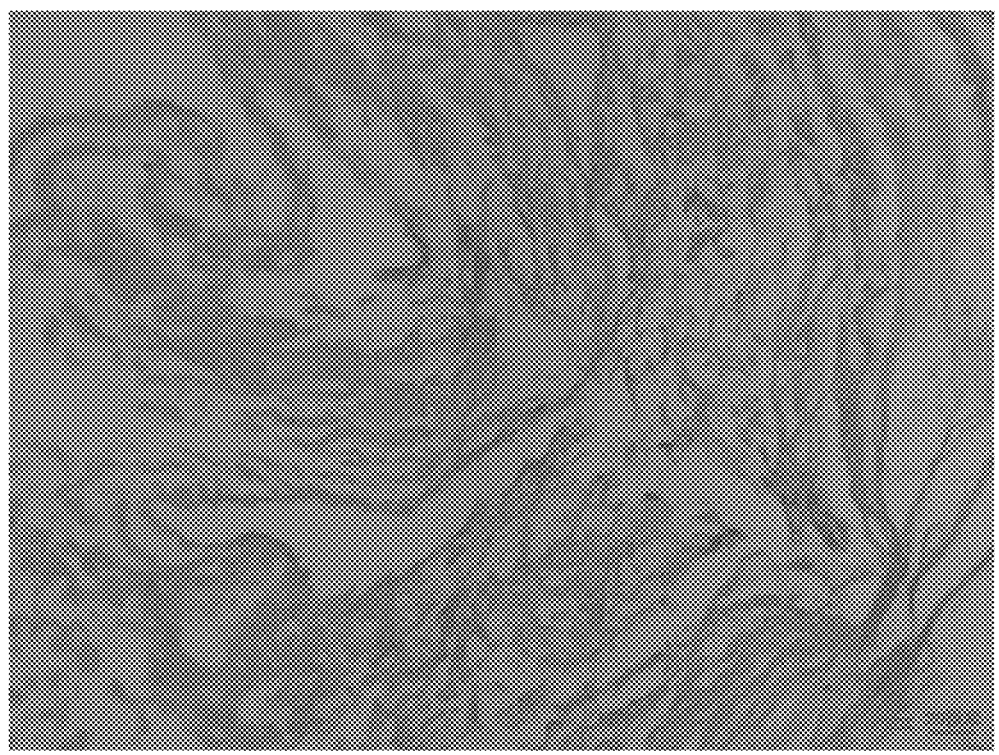
FIG. 2 is an optical microscope view of the second embodiment.

1) Observation through optical microscopy: the material is coated with paraffin and the material is colored with hematoxylin-eosin staining. The coated and colored material is observed in the optical microscopy through inverted phase contrast microscope. As shown in FIG. 2, there is no residue of cell-free and cell debris, collagen is in a row under the microscopy.

Figure 3:
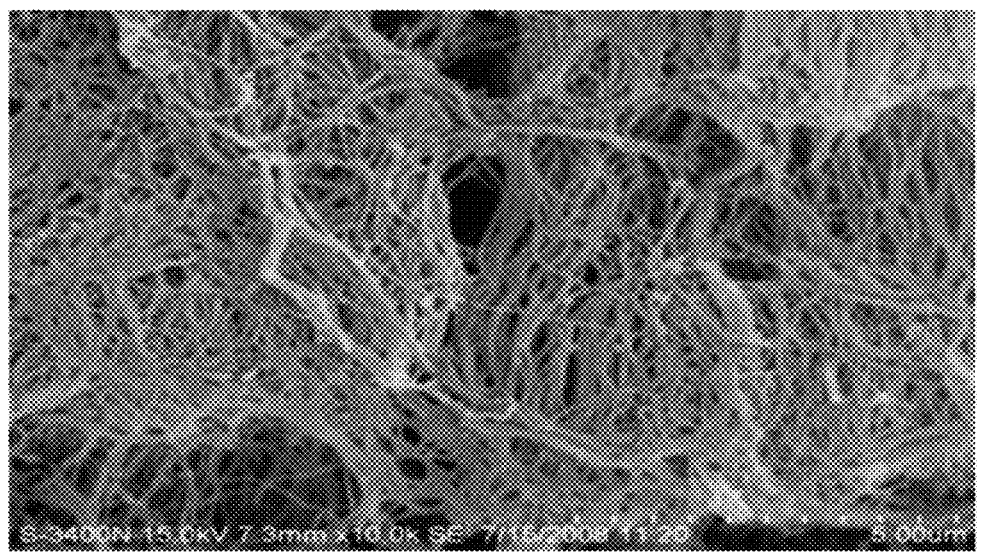
FIG. 3 is an electron microscopy ultramicro structure of the second embodiment.

2) Ultrastructural observation. Results: the material is porous, fibre without fracture, pore size, average pore size of 200 um, the porosity is greater than 85%, as shown in FIG. 3.

4. Growth Factor

Every 6 cm$^2$ samples should mix up with 1 ml extraction medium; the preparation of the testing liquids is conducted under the temperature of 37±1° C. for 72±2 hours. The extraction medium is saline solution. Growth factor (bFGF) and vascular endothelial growth factor (VEGF) levels in the extraction medium are detected by ELLISA method. Results show that the level of bFGF is 121.8±2.683 ng/L and VEGF is 93.8±3.033 ng/L.

5. Biological property testing is conducted, wherein the testing items include cytotoxicity, delayed-type hypersensitivity, and skin reaction.

1) Cytotoxicity: method: every 6 cm² samples should mix up with 1 ml extraction medium. The preparation of the testing liquids is conducted under the temperature of 37±1° C. for 24±2 hours. The extraction medium is MEM serum-containing medium. The testing experiment is conducted following the regulation published in GB/T 16886.5-2003, such as the biological evaluation of medical devices part 5: in vitro cytotoxicity test. Result shows that the toxicity of cell is less than or equal to the grade 1.

2) Delayed-Type Hypersensitivity:

Every 6 cm² samples should mix up with 1 ml extraction medium. The preparation of the testing liquids is conducted under the temperature of 37±1° C. for 72±2 hours. The extraction medium is saline extract and cottonseed oil. The testing experiment is conducted following the regulation published in GB/T 16886.10-2005 (the biological evaluation of medical devices part 10th: stimulating and delayed-type hypersensitivity test). Results show that there is no delayed-type hypersensitivity reaction.

3). Intradermal reaction: the corresponding proportion between the leaching medium and the samples is that every 6 cm samples should be mixed with 1 ml leaching medium. The experiment is conducted under the temperature of 37±1° C. It takes 72±2 hours to prepare the leaching medium. The leaching medium is saline or cottonseed oil. The experiment is conducted following the regulations of GB/T 16886.10 2005 (the biological evaluation of medical devices part 10: stimulation and delayed-type hypersensitivity test). Results: the average comparison score between the tested sample and the solvent is less than 1.0.

The Third Embodiment

The preparation of cell-free pig dermal matrix material. Freshly slaughtered pig dermal tissue is taken as raw material. The preparation method is the same as the first embodiment.

The Fourth Embodiment

Testing the performance (physical and chemical properties, histology, growth factors and biology) of the cell-free pig dermal matrix material obtained from the third embodiment. The testing method is the same as stated in the second embodiment. Results show that the suture tensile strength of the decellularized dermal matrix material obtained from the third embodiment is greater than 5 N. The transverse and longitudinal tensile strength are greater than 20 N. The bursting strength is greater than 120N and the porosity is larger than 80%. The copy number of the viral DNA is 0. The endotoxin content is less than 5 eu/g and the amount of DNA residual does not exceed 150 pg/g. There is no delayed-type hypersensitivity or intradermal reaction occurring.

The Fifth Embodiment

Preparation of the decellularized pig pericardium substrate materials.

Freshly slaughtered pig's pericardial tissue is taken as raw material. Preparation method is the same as stated in the first embodiment.

The Sixth Embodiment

Testing the performance (physical and chemical properties, histology, growth factors and biological) of the decellularized pig pericardium substrate materials obtained from the fifth embodiment. The testing method is the same as stated in the second embodiment.

Results show that the suture tensile strength of the decellularized pig pericardium substrate materials obtained from the fifth embodiment is greater than 5 N. The transverse and longitudinal tensile strength are greater than 20 N. The bursting strength is greater than 120N and the porosity is larger than 85%. The copy number of the viral DNA is 0. The endotoxin content is less than 5 EU/g and the amount of DNA residual does not exceed 150 pg/g, there is no delayed-type hypersensitivity or intradermal reaction occurring.

The above embodiments are the descriptions of this invention. This invention should cover all equivalent modifications and combinations of these embodiments, and is not limited to the above embodiments.

The invention claimed is:

1. A preparation method for an implantable medical biological material of animal origin, comprising the following steps:
   step 1, pre-processing, separating and washing of animal tissue material
   taking out fresh animal tissue and washing the flesh animal tissue with injection water for 3 times to obtain washed animal tissue;
   step 2; inactivating virus
   inactivating the virus in the washed animal tissue obtained in the step 1 by using ethanol solution with a low concentration of peracetic acid to obtain inactivated material;
   conducting a cleaning step in an oscillation ultrasonic cleaner at a constant temperature;
   wherein the peracetic acid takes up a percentage of 0.05~0.2% by volume, an inactivation time ranges from 1 h to 2 hours;
   wherein the constant temperature ranges from 4° C. to 40° C.;
   cleaning the inactivated material in a phosphate buffer solution for 2~5 times;
   wherein each time the cleaning lasts for 15 minutes;
   detecting a pH value of the phosphate buffer solution after each time of the cleaning:
   when a pH value reaches a range from 6.5 to 7.5, cleaning the inactivated material with flow injection water until a conductivity is lower than 1.5 um/s, such that a first cleaned material is obtained;
   step 3, decellularizing cell
   wherein the step 3 is conducted in an oscillation sink having an ultrasonic cleaner at a constant temperature;
   placing the first cleaned material obtained in the step 2 into the oscillation sink;
   injecting a sodium hydroxide solution into the oscillation sink, and turning on the ultrasonic cleaner;
   wherein a cleaning time by using the sodium hydroxide solution ranges from 5 to 30 minutes:
   wherein a concentration of the sodium hydroxide solution ranges from 5 mmol/L to 100 mmol/L;
   turning off the ultrasonic cleaner;
   pouring out the sodium hydroxide solution;
   injecting a phosphate buffer solution into the ultrasonic cleaner and turning on the ultrasonic cleaner;
   wherein a cleaning time by using the phosphate buffer solution ranges from 5 minutes to 20 minutes;
   repeating the cleaning with the sodium hydroxide solution for 2~5 times to obtain a second cleaned material;
   detecting a pH value of the phosphate buffer solution after each time of the cleaning;

cleaning the second cleaned material by using a flowing injection water when the pH value of the phosphate buffer solution is in a range from 6.5 to 7.5;
terminating the cleaning until a conductivity is lower than 1.5 um/s;
step 4, sodium chloride treating
wherein the step 4 is conducted in the oscillation sink having the ultrasonic cleaner at a constant temperature;
injecting a sodium chloride solution into the oscillation sink, and turning on the ultrasonic cleaner to obtain a third cleaned material;
wherein a cleaning time by using the sodium chloride solution ranges from 5-30 minutes;
wherein a concentration of the sodium chloride solution is 0.015 mol/L or 2 mol/L, and a pH value of the sodium chloride solution is less than 7.8;
washing the third cleaned material with the flowing injection water until a conductivity is lower than 1.5 um/s, such that a fourth cleaned material is obtained;
step 5, molding step
fixing the fourth cleaned material obtained in the step 4 to a plurality of devices,
freezing and drying the fourth cleaned material, and drilling a plurality of micro holes on the fourth cleaned material using a laser;
wherein sizes and shapes of the plurality of devices vary in accordance with different product requirements;
securing the fourth cleaned material onto the plurality of devices and washing the fourth cleaned material by flowing injected water, such that a washed material is obtained;
placing the washed material into a freeze drying machine and securing;
performing a pre-designed lyophilization process to obtain a lyophilized material;
wherein the pre-designed lyophilization process includes
pre-cooling the washed material to a temperature of −25~50° C., and keeping the temperature for 0.5~4 hours;
rising the temperature to 15° C. and keeping the temperature for 4~12 hours;
rising the temperature to 15° C. and keeping the temperature for 0.5~4 hours;
rising the temperature to 25° C. and keeping the temperature for 4 hours;
drilling a plurality of micro holes on the lyophilized material using a laser such that a drilled material is obtained:
wherein a diameter of each of the plurality of micro holes of the drilled material ranges from 0.05 to 1 mm;
wherein a distance between adjacent micro holes ranges from 0.1 cm to 2 cm:
step 6, packaging sterilization
performing a packaging step in a sterile condition;
wherein a first layer of a packaging is a tyvek paper, a second layer of the packaging is a polyethylene plastic layer;
performing an ethylene oxide sterilization after the packaging step.

2. The preparation method for the implantable medical biological material of animal origin of claim 1, wherein the animals is selected from the group consisting of pigs, cows and horses.

3. The preparation method for the implantable medical biological material of animal origin of claim 1, wherein the fresh animal tissue is selected from the group consisting of small intestinal submucosa, leather and pericardium.

4. The preparation method for the implantable medical biological material of animal origin of claim 1, wherein the percentage of the acetic acid peroxide in the step 2 is 0.1% by volume.

5. The preparation method for the implantable medical biological material of animal origin of claim 1, wherein a inactivating time in the step 2 is 1 hour.

6. The preparation method for the implantable medical biological material of animal origin of claim 1, wherein an oscillation frequency of the oscillation sink in the steps 3 and 4 is 100~300 RPM.

7. The preparation method for the implantable medical biological material of animal origin of claim 6, wherein the oscillation frequency of the oscillation sink in the steps 3 and 4 is 200 RPM.

8. The preparation method for the implantable medical biological material of animal origin of claim 1, wherein an ultrasonic frequency of the ultrasonic cleaner in the steps 3 and 4 is 20~80 kHz.

9. The preparation method for the implantable medical biological material of animal origin of claim 8, wherein an ultrasonic frequency of the ultrasonic cleaner in the steps 3 and 4 is 45 kHz.

10. The preparation method for the implantable medical biological material of animal origin of claim 1, wherein the cleaning time by using the sodium chloride solution in the step 4 is 20 mins.

11. The preparation method for the implantable medical biological material of animal origin of claim 1, wherein the concentration of the sodium chloride solution in the step 4 is 5-20 mmol/L.

12. The preparation method for the implantable medical biological material of animal origin of claim 11, wherein the concentration of the sodium chloride solution in the step 4 is 10 mmol/L.

13. The preparation method for the implantable medical biological material of animal origin of claim 1, wherein the cleaning time for the material by using the phosphate buffer solution in the step 3 is 15 min.

14. The preparation method for the implantable medical biological material of animal origin of claim 1, wherein a cleaning time for the material by using the sodium hydroxide solution in the step 3 is 20 min.

15. The preparation method for the implantable medical biological material of animal origin of claim 1, wherein the concentration of the sodium hydroxide solution in the step 3 is 0.015 mol/L.

16. The preparation method for the implantable medical biological material of animal origin of claim 1, wherein the plurality of devices in the step 5 are stainless steel devices.

17. The preparation method for the implantable medical biological material of animal origin of claim 1, wherein the pre-designed lyophilization process in the step 5 further comprises:
pre-cooling the washed material to a temperature of 25° C. and keeping the temperature for 2 hours;
rising the temperature to 15° C. and keeping the temperature for 8 hours;
rising the temperature to 15° C. and keeping the temperature for 2 hours;
rising the temperature to 25° C. and keeping the temperature for 4 hours.

18. The preparation method for the implantable medical biological material of animal origin of claim 1, wherein the diameter of each of the plurality of micro holes drilled by the laser in the step 5 ranges from 0.2 to 0.5 mm.

19. The preparation method for the implantable medical biological material of animal origin of claim 1, wherein the distance between adjacent micro holes drilled by the laser in the step 5 ranges from 0.5 to 1 cm.

20. The preparation method for the implantable medical biological material of animal origin of claim 1, wherein the fresh animal tissue is selected from the group consisting of small intestine tissue, dermal tissue, and pericardial tissue.

* * * * *